United States Patent [19]
Noren et al.

[11] Patent Number: 5,405,364
[45] Date of Patent: Apr. 11, 1995

[54] METHOD AND ARRANGEMENT FOR CALCULATING A PHYSIOLOGICAL FUNCTION PARAMETER OF A LIFE FORM FOR THERAPY CONTROL

[75] Inventors: Kjell Noren, Solna; Agneta Franksson, Stockholm; Kenth-Åke-Sune Nilsson, Akersberga, all of Sweden

[73] Assignee: Siemens Aktiengesellschaft, Munich, Germany

[21] Appl. No.: 72,432

[22] Filed: Jun. 7, 1993

[30] Foreign Application Priority Data

Jun. 9, 1992 [EP] European Pat. Off. ............ 92109688

[51] Int. Cl.6 ............................................. A61N 1/365
[52] U.S. Cl. ..................................................... 607/17
[58] Field of Search ............... 128/670, 671, 696, 697, 128/698, 700, 901; 607/17

[56] References Cited

U.S. PATENT DOCUMENTS

| | | | |
|---|---|---|---|
| 3,762,397 | 10/1973 | Cage | 128/700 |
| 3,848,584 | 11/1974 | Suzuki et al. | 128/901 |
| 4,027,657 | 6/1977 | Sureau et al. | 128/698 |
| 4,243,045 | 1/1981 | Maas | 128/696 |
| 4,248,240 | 2/1981 | van Eykern | 128/671 |
| 4,381,786 | 5/1983 | Duggan | 128/696 |
| 4,399,820 | 8/1983 | Wirtzfeld et al. | 128/419 PG |
| 4,408,615 | 10/1983 | Grossman | 128/696 |
| 4,494,551 | 1/1985 | Little, III et al. | 128/696 |
| 4,702,253 | 10/1987 | Nappholz et al. | 128/419 PG |
| 4,823,797 | 4/1989 | Heinze et al. | 128/419 PG |
| 4,830,020 | 5/1989 | Ruth | 128/901 |
| 4,899,760 | 2/1990 | Jagb et al. | 128/696 |
| 4,940,053 | 7/1990 | Mann et al. | 128/419 PG |
| 4,958,640 | 9/1990 | Logan | 128/671 |
| 5,010,887 | 4/1991 | Thornander | 128/901 |
| 5,025,784 | 6/1991 | Shao et al. | 128/700 |
| 5,105,354 | 4/1992 | Nishimura | 128/671 |

FOREIGN PATENT DOCUMENTS

| | | |
|---|---|---|
| 0249819 | 12/1987 | European Pat. Off. . |
| 0249824 | 12/1987 | European Pat. Off. . |
| 0249825 | 12/1987 | European Pat. Off. . |
| 0331309 | 9/1989 | European Pat. Off. . |
| 0392800 | 10/1990 | European Pat. Off. . |
| 0447024 | 9/1991 | European Pat. Off. . |
| 0059868 | 9/1992 | European Pat. Off. . |

Primary Examiner—William E. Kamm
Attorney, Agent, or Firm—Hill, Steadman & Simpson

[57] ABSTRACT

A method and apparatus for calculating a parameter for a physiological function wherein, given a measurement signal influenced by more than one physiological function parameter, signal components of the measurement signal arising from a parameter not of interest are filtered out such that a period duration inversely proportional to the respective current frequency of the parameter not of interest is continuously identified and a mean value of the measurement signal is continuously formed over the identified period duration.

14 Claims, 2 Drawing Sheets

METHOD AND ARRANGEMENT FOR CALCULATING A PHYSIOLOGICAL FUNCTION PARAMETER OF A LIFE FORM FOR THERAPY CONTROL

BACKGROUND OF THE INVENTION

The invention relates to a method for calculating a physiological function parameter of a life form, whereby a measurement signal, which changes depending on the function parameter, is acquired with a measuring instrument, and whereby signal components of the measurement signal relating to another parameter that likewise influences the measured signal and having a characteristic frequency are separated out from the measurement signal by filtering. The invention is also directed to a corresponding arrangement, i.e., an apparatus, for calculating the physiological function parameter.

One such method is disclosed in U.S. Pat. No. 4,702,253, the teachings of which are incorporated by reference. The disclosed method is employed for identifying the respiratory activity of a patient.

In the disclosed method, blood impedance, which changes in view of patient respiration and in view of patient heart activity, is measured using electrodes arranged in the region of the heart of the patient and using a measuring instrument connected to the electrodes. A measurement signal generated by the measuring instrument is sampled by means of a sampling stage utilizing a sampling frequency of 100 Hz and the samples are supplied to a filter stage in which low-frequency signal components in the range from 0.05 Hz through 1 Hz are filtered out of the measurement signal. This filtering is supposed to remove signal components that relate to respiration. The respiration minute volume subsequently is identified from the filtered-out, low-frequency signal components and is utilized for frequency control of a heart pacemaker.

In the disclosed method, the extraction of the low-frequency signal components is undertaken with a band-pass filter having fixed limit frequencies. However, what is thereby left out of consideration is that the respiratory frequency can vary over a frequency range from approximately 0.09 Hz through 1.1 Hz, depending on the physical stress or emotional mood of the patient, and that the heart frequency can vary in a range from approximately 0.9 Hz through 2.5 Hz. The two frequency ranges thus overlap, so that the signal components utilized for the calculation of the respiration minute volume not only depend on the respiration but also depend on the heart activity, particularly given low heart beat frequencies. This can give rise to inaccurate calculations.

SUMMARY OF THE INVENTION

The present invention provides that in a measurement signal which changes depending on more than one function parameter of a life form, signal components relating to a function parameter not of interest effectively are filtered out of the measurement signal, even when the frequency of the function parameter not of interest varies.

In an embodiment, the invention provides a method wherein a period inversely proportional to a current frequency of the function parameter not of interest is continuously calculated, and that a mean value of the measurement signal is continuously calculated over the period of the parameter not of interest so that the signal components based on the function parameter not of interest effectively are separated or filtered out of the measurement signal.

As a result, a chronological curve of the mean value formed in this way corresponds to a notch filtered version of the measurement signal, whereby the frequency range suppressed by the filtering continuously adapts to the current frequency of the signal components to be suppressed. As an example, the 50/60 Hz unwanted signals induced by an alternating current network can be filtered out of an electrocardiogram in this way.

When the parameter not of interest (i.e., that parameter whose signal components are to be filtered out) is made up of individual events which repeat with a characteristic frequency, the events themselves advantageously are detected, whereby the respective current period of the parameter not of interest is calculated from the chronological distance between the two most recently detected events. For example, when the respiratory activity of the patient is to be measured on the basis of the impedance measurement, the influences that can be filtered out of the impedance measurement signal, in accordance with the method of the invention, can be influences from events such as heart beats, arm motions, pressure signals.

Moreover, the events advantageously are detected with a detector means that is separate from the measuring instrument. Thus, for example, heart beats can be detected by a heart beat detector such as, for example, a QRS detector, or arm motions can be detected by a motion sensor with reference to the aforementioned impedance measurement.

Alternatively, signal components correlating to the events can be filtered out of the measurement signal and can be evaluated for detection of the events. Such a filtering can ensue with some relatively simple means because only the events as such are to be detected, whereas the filtering out of the measurement signal of the signal components correlating to the events ensues on the basis of the mean value formation method of the invention.

The formation of the mean value advantageously is simplified such that the measurement signal is sampled with a prescribed or known sampling frequency, and such that the mean value is formed from the sum of samples acquired during the period calculated for the parameter not of interest in relationship to the number of samples. This also takes into account the possibility that the sampling frequency varies depending on the identified period or that the plurality of samples remains constant with reference to the period.

In order to prevent the plurality of samples utilized for forming the mean value from suddenly changing given a change of the spacing or timing between two successive events, in an embodiment of the invention it is provided that the plurality of samples acquired after the detection of an event and between this event and the preceding event is recalculated, and that the plurality of samples respectively utilized for the formation of the mean value for the following sampling times is adapted step-by-step to the newly calculated value proceeding from a valid value calculated before the detection event.

The calculating outlay required for the formation of the mean values of the samples advantageously can be reduced to a minimum in that a counter reading of a counter can be incremented at every sampling time, in that the counter reading can be transferred into a pointer register at the first sampling time after the detection of an event and then be reset to zero, in that the current sample can be read into a shift register at every sampling time, whereby the memory contents of the shift register are respectively shifted by one storage location in the shift direction, and in that the mean value of the sum of the memory contents of the first storage location as viewed in the shift direction up to the storage location identified by the content of the pointer register can be calculated in relationship to the content of the pointer register in a calculating unit for every sampling time.

A possible, discontinuous change in the plurality of samples utilized for the formation of the mean value after the appearance of an event thereby can be avoided in that the counter reading can be intermediately stored at the respective first sampling time after the detection of an event and compared to the content of the pointer register, and in that the content of the pointer register can be adapted step-by-step to the intermediately stored counter reading at the following sampling times.

The plurality of the storage locations of the shift register can be defined by the ratio of the sampling frequency to the lowest anticipated event frequency (for example, heart beat frequency), so that the storage capacity of the shift register is adequate for forming the samples even given extremely low event frequencies.

In an embodiment, the invention provides an arrangement, i.e., an apparatus, for identifying a physiological function parameter of a life form comprising measuring means for forming a measurement signal which changes depending on respiration as well as heart activity, means connected to the measuring means for sampling the measurement signal at a prescribed sampling frequency, and filter means following the sampling means for separating out of the measurement signal low-frequency signal parts corresponding to the respiration.

In an embodiment of the invention, the arrangement comprises a heart beat detector, the filter means includes a shift register into which samples are successively read, a calculating unit is connected to the shift register and has selective access to contents of the memory of the storage locations of the shift register, the heart beat detector is connected to a reset input of a counter whose counting input is charged with a sampling frequency, a pointer register is connected to the heart beat detector via a control input and accepts a counter reading of the counter given the occurrence of a heart beat and is connected to an output of the counter, and the calculating unit is connected to the output of the pointer register and generates a mean value at every sampling time, the mean value being formed from a sum of the contents of the memories of the storage locations of the shift register, from the first storage location, as viewed in the shift direction, to the storage location referenced by the content of the pointer register, in relationship to the content of the pointer register.

In an embodiment of the invention, the arrangement preferably is a component part of a heart pacemaker in which the mean values calculated at every sampling time are utilized for controlling the heart pacemaker frequency.

These and other features of the invention are discussed in greater detail below in the following detailed description of the presently preferred embodiments with reference to the accompanying drawings.

DETAILED DESCRIPTION OF THE PRESENTLY PREFERRED EMBODIMENTS

As discussed above, the invention provides a method and apparatus for separating out of a measurement signal, low frequency components that relate to life form function parameters not of concern. The method and apparatus are described below with reference to accompanying FIGS. 1-4.

Figure 1:
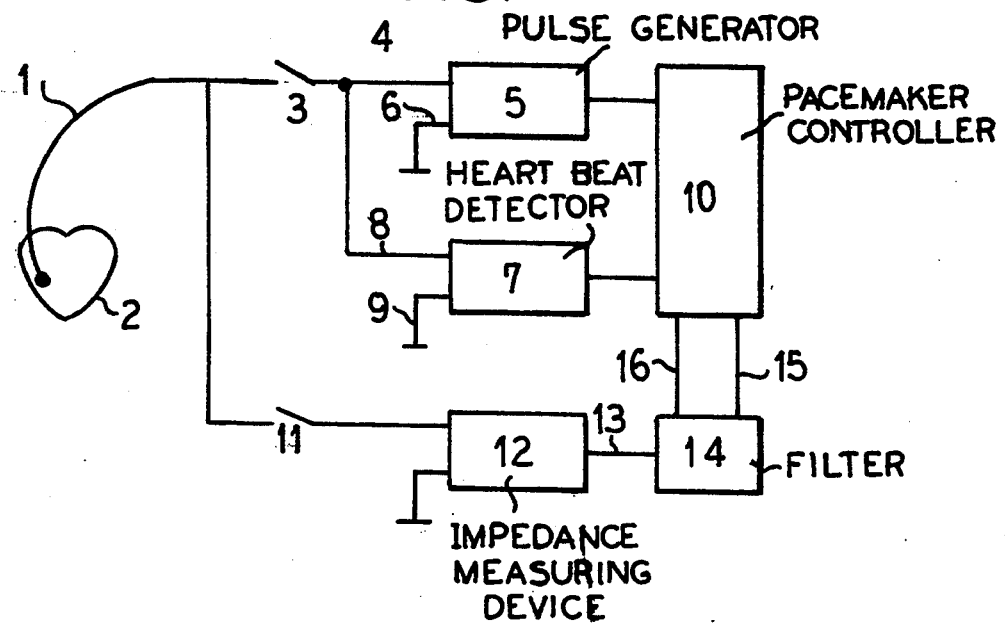
FIG. 1 illustrates a block circuit diagram of a frequency-controlled heart pacemaker that comprises a measuring instrument for forming a measurement signal that changes depending on patient respiration and on patient heart activity.

FIG. 1 illustrates a block circuit diagram of a frequency-controlled heart pacemaker from which an electrode 1 leads to a heart 2 of a patient. The electrode 1 is connected via a controllable switch 3 to an output terminal 4 of a stimulation pulse generator 5 via a controllable switch 3. A second output terminal 6 of the stimulation pulse generator 5 is connected to the housing (not shown here) of the heart pacemaker.

A heart beat detector 7 having a first input terminal 8 connected to the output terminal 4 of the stimulation pulse generator 5 and having a second input terminal 9 likewise connected to the heart pacemaker housing also is provided. The stimulation pulse generator 5 and the heart beat detector 7 then are both connected to a heart pacemaker control 10 that starts a base time interval after every stimulated or detected, natural heart beat and that triggers the output of a stimulation pulse by the stimulation pulse generator 5 when the base time interval expires without a natural heart beat having been detected by the heart beat detector 7.

A measuring instrument 12 for measuring the impedance of the body tissue between the electrode 1 and the heart pacemaker housing (not shown) is connected to the electrode 1 via a further switch 11 and to the reference potential terminal formed by the heart pacemaker housing. This instrument 12 produces an analog measurement impedance signal which changes both depending on the respiration of the patient as well as on the patient's heart activity.

As can be appreciated, the stimulation pulse generator 5 with the heart beat detector 7 and the measuring instrument 12 can be connected to the electrode 1 separately from one another with the assistance of the switches 3 and 11, respectively, so that they cannot mutually influence one another.

As further illustrated, the analog measurement signal of the measuring instrument 12 is supplied to a filter arrangement 14 via an output line 13 in the filter arrangement 14. Low-frequency signal components correlating to the respiration are separated out of the measured signal and then are supplied via a control line 15 to the heart pacemaker control 10 wherein the base time interval is varied depending on the respiration of the patient.

In the exemplary embodiment shown in FIG. 1, the stimulation of the heart 2, the detection of heart beats, and the impedance measurement each respectively ensue between the electrode 1 and the heart pacemaker housing. Alternatively, of course, it is possible to provide a multi-pole electrode system and to undertake the stimulation, detection and measurement between the individual electrodes of the multi-pole electrode system. In addition to the respiration-dependent control, the base time interval in the heart pacemaker control 10 can also be controlled so as to be dependent on the higher-frequency signal components of the measurement signal that correlate with the heart activity. Other physiological parameters of the heart such as, for example, pressure and flow can also be acquired instead of the impedance and utilized for controlling the heart pacemaker.

As FIG. 1 illustrates, the filter arrangement 14 is connected via a control line 16 to the heart pacemaker control 10 which generates a control signal on the control line 16 every time the stimulation pulse generator 5 stimulates the heart beat or the heart beat detector 7 detects a natural heart beat. However, it is also possible to filter components relating to the individual heart beat events out of the measurement signal of the measuring instrument 12 with high-pass filtering.

Figure 2:
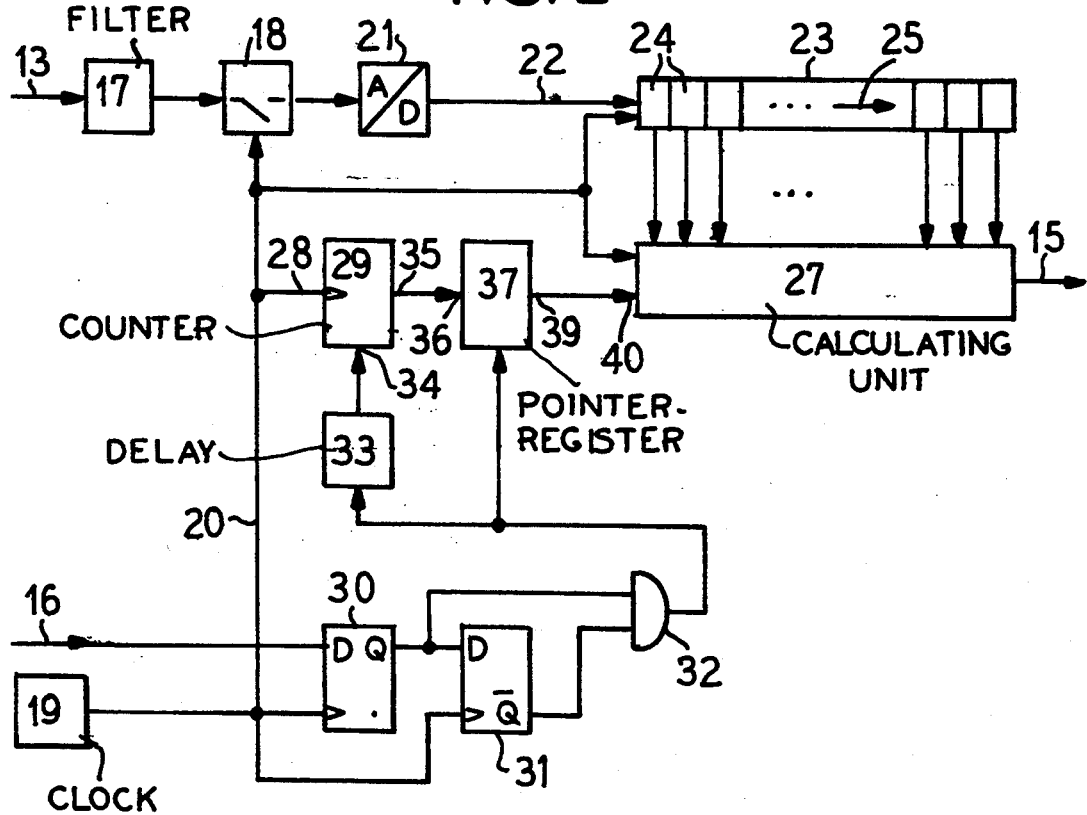
FIG. 2 illustrates a block circuit diagram of a filter arrangement for separating out of the measurement signal low-frequency signal components corresponding to patient respiration.

FIG. 2 illustrates a more detailed block circuit diagram of the filter arrangement 14. As illustrated, the analog measurement signal proceeds via the output line 13 of the measuring instrument 12 onto a low-pass or band-pass filter 17 and proceeds from the latter to a sampling means 18 wherein the measurement signal is sampled with a sampling frequency of, for example, 10 Hz that is generated by a clock generator 19 and is supplied via a clock signal line 20 to the sampling means 18. The analog samples are converted into corresponding digital values in an analog-to-digital converter 21 that follows the sampling means 18 and are read into a shift register 23 at the rate of the sampling frequency via a data signal line 22, whereby the memory contents of the storage locations 24 of the shift register 23 are respectively shifted by one storage location 24 in the direction of the arrow 25 at every new read-in of a sample. The plurality of storage locations 24 of the shift register 23 preferably derives from the relationship of the sampling frequency to the lowest anticipated heart beat frequency and consequently can amount to, for example, "20" given a sampling frequency of 10 Hz and a minimum heart beat frequency of 30 beats per minute. The individual storage locations 24 are connected via output signal lines 26 to a calculating unit 27 that selectively accesses the memory contents of the storage locations 24 at the rate of the sampling frequency and operates on the samples obtained in this way to form a mean value on the control line 15, as set forth in greater detail below.

The clock signal line 20 is connected to the counting or trigger input 28 of a counter 29 whose counter reading is incremented in the clock of the sampling frequency, i.e. at every sampling event. The control line 16 is connected to a trigger input D and the clock generator 19 is connected to the clock input of a D flip-flop 30 which forms a synchronous monoflop together with a following, further D flip-flop 31 and an AND gate 32 connected to the non-inverting output Q of the first D flip-flop 30 and to the inverting output Q of the second D flip-flop 31. The output of the AND gate 32 is connected via a delay element 33 to a reset input 34 of the counter 29. The output 35 of the counter 29 is connected to the input 36 of a pointer register 37, which comprises a control input 38 connected to the output of the AND gate 32 and whose output 39 is connected to a control input 40 of the calculating unit 27.

Figure 3:
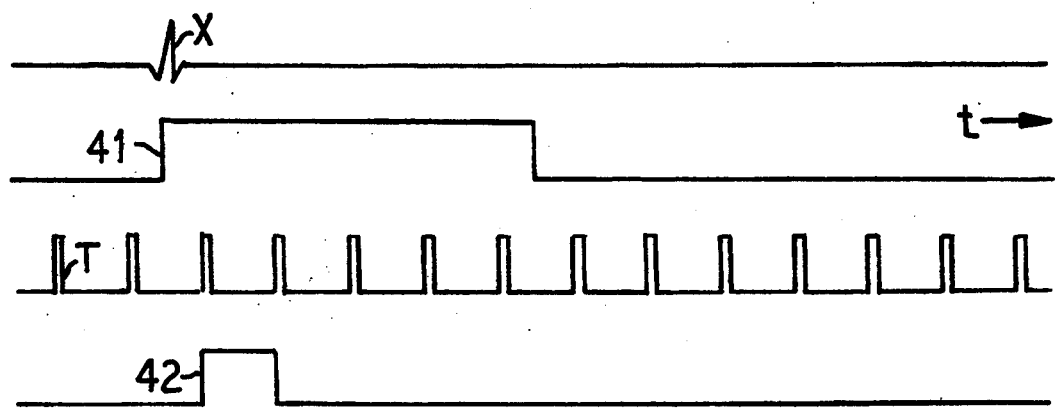
FIG. 3 illustrates a timing diagram for signals in the filter arrangement shown in FIG. 2.

As FIG. 3 illustrates, a control signal 41 is generated by the heart pacemaker control 10 on the control line 16 after the occurrence of a stimulated or detected heart beat X; the length of this control signal 41 is at least slightly longer than the spacing between two sampling times prescribed by the sampling clock T of the clock generator 19. The synchronous monoflop comprised of elements 30, 31 and 32 generates a signal 42 at the output of the AND gate 32 at the first sampling time after the appearance of the heart beat X, this signal 42 ending no later than the next-successive sampling time. The leading edge of the signal 42 thus marks the respective first sampling time following a heart beat X. If further heart beats X appear during the duration of the control signal 41, then this is not registered by the synchronous monoflop comprised of elements 30, 31 and 32. The duration of the control signal 41 thus corresponds to a refractory time within which a misdetection of heart beats for the filtering of the impedance signal is avoided.

With the appearance of the signal 42, the counter reading of the counter 29 is accepted by the pointer register 37 before the counter 29 is reset after a short delay. At every sampling time that is communicated to it via the clock signal line 20, the calculating unit 27 generates a mean value on the control line 15, this mean value being composed of the sum of the memory contents of the first storage location 24 as seen in the shift direction 25 up to the storage location 24 identified by the content of the pointer register 37 divided by the content of the pointer register 37.

Figure 4:
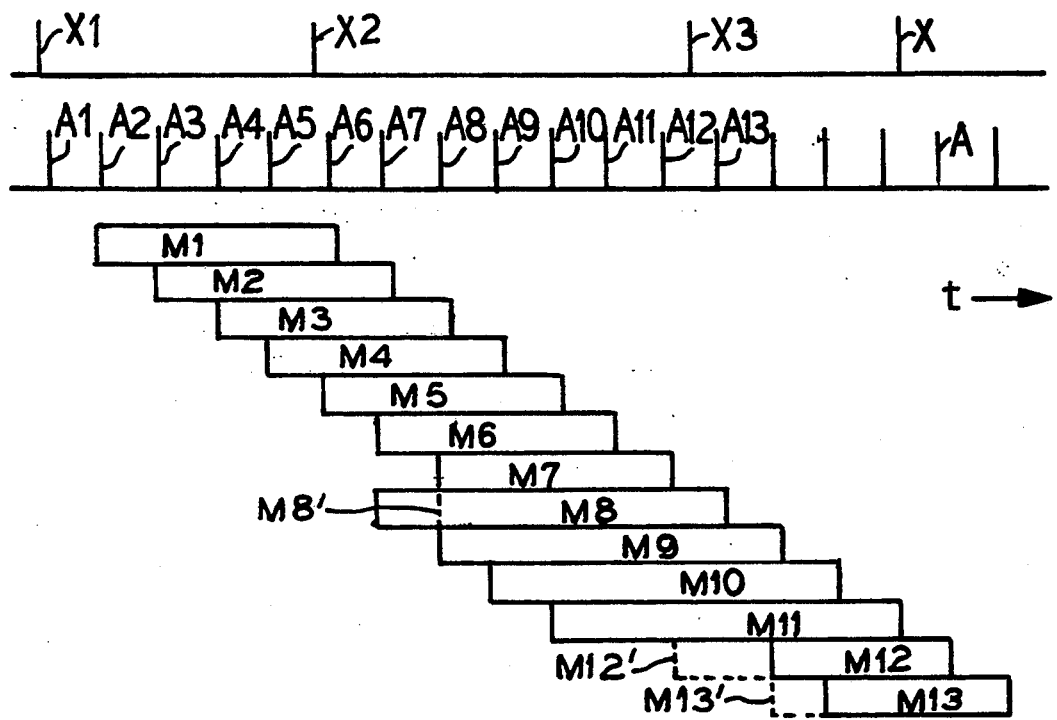
FIG. 4 illustrates a diagram of samples of the measurement signal that are utilized depending on stimulated and detected heart beats for forming mean sample values at the output of the filter arrangement.

With reference now to FIG. 4, the function of the presently preferred filter arrangement 14 is explained, the appearance of stimulated or detected heart beats X being shown in the uppermost line of FIG. 4 depending on time t. The samples A that occur on the data signal line 22 are shown in the line below this. The samples A, of course, vary (i.e., the amplitudes vary) depending on the heart activity and on the respiratory activity of the patient and are respectively marked here as strokes of equal length only for reasons of simplification. The illustrated relationship of the spacings between successive heart beats X with reference to the spacing between two successive sampling times also is arbitrarily selected here.

At the first sampling time A1 after the occurrence of the first heart beat X1, the counter reading of the counter 29 is reset to zero and the current sample A1 is read into the shift register 23. At every further sampling time, a respective new sample A2 through, e.g., A5 is read into the shift register 23 and the counter reading is incremented every time.

At the first sampling time following the next heart beat X2, the sample A6 is read into the shift register 23 and the counter is incremented to the counter reading "5". The counter reading "5" then is transferred into the pointer register 37 and the counter 29 is reset to zero.

The memory contents of the storage locations 24, starting from the first memory location seen in shift direction up to the fifth storage location indicated by the content of the pointer register 37, then are added up in the calculating unit 27, so that the sum S=A6+A5+A4+A3+A2 is obtained. The sum S is divided by the content of the pointer register 37, so that the mean value M1=(A6+A5+A4+A3+A2)/5 appears on the control line 15. In FIG. 4, the mean value M1 is marked by a bar or block that covers or spans the samples A2 through A6 taken into consideration in the formation of the mean value M1.

At the next sampling time, a new mean value M2 is formed from the sum of the newly added sample A7 and the earlier samples A6 through A3 divided by the content "5" of the pointer register 37. At the same time, the counter reading of the counter 29 is incremented. A respectively new mean value is formed in the same way for every following sampling time until the timing between occurrences of heat beats varies. Consequently, a mean value M7=(A12+A11+A10+A9+A8)/5 is derived for the last sampling time before the third heart beat X3. The counter reading of the counter 29 at this time amounts to "6".

At the next sampling time that follows as the first following the third heart beat X3, the sample A13 is read into the shift register 23, the counter reading of the counter 29 is incremented to "7" due to the increase in timing between the heart beat X3 and the heart beat X2 and is transferred into the pointer register 37, and the counter 29 is subsequently reset to zero. For a new mean value M8, the memory contents of the first storage location up to the seventh storage location indicated by the content of the pointer register 37 are summed up and divided by the number 7 in the pointer register 37, so that M8=(A13+A12+A11+A10+A9+A8+A7)/7 is valid. The next mean values M9 through M13 and all further mean values are calculated in a corresponding way.

As FIG. 4 illustrates, with respect to the mean values M8 and M12, greater discontinuities in the plurality of samples with reference to the respective preceding mean values M7 and M11 can be taken into consideration for the mean value formation. These discontinuities can be avoided in that the plurality of samples to be taken into consideration are respectively matched or adjusted to the new value step-by-step proceeding from the respective earlier value, as illustrated in FIG. 4 by the broken-line bars M8' and M9' or, respectively, M12' and M13'.

With reference to the example illustrated by the block circuit diagram of FIG. 2, the foregoing can occur in such a way that the count value transferred from the pointer register 37 into the calculating unit 27 is compared to a count value previously intermediately stored in the calculating unit 27. When the difference is less than 2, then the new count value from the pointer register 37 is intermediately stored in the calculating unit 27 instead of the prior count value. When, by contrast, the difference is greater than or equal to 2, then the previously intermediately stored count value is varied in the direction toward the new count value by one or by some other prescribed number and is then intermediately stored. The respective intermediately stored count value is employed for the calculation of the plurality of samples in the sum formation and for the following division. At every sampling time following the occurrence of a heart beat, the plurality of samples to be taken into consideration in the calculation of the mean value is adapted in this way from the earlier value in the pointer register 37 to the new value in the pointer register 37.

For example, and with reference to the adjusted calculation of the mean value M8' in FIG. 4, when sample $A_{13}$ is stored in the shift register, the current pointer register will be "7" and the intermediately stored current value will be "5". Since "7" is greater than "5" at least by the arbitrarily selected difference of "2", the prior value of "5" is used in determining the samples used in generating the mean value M8'.

Although modifications and changes may be suggested by those skilled in the art, it is the intention of the inventors to embody within the patent warranted hereon all changes and modifications as reasonably and properly come within the scope of their contribution to the art.

We claim:

1. A method for measuring a parameter of interest of a physiological function of a life form, comprising the steps of:
   (a) sensing a physiological function and generating a measurement signal including signal components relating to occurrences of events of a parameter not of interest;
   (b) producing a succession of samples of the measurement signal by sampling the measurement of signal at a frequency greater than a frequency of the occurrences of the events of the parameter not of interest;
   (c) measuring at least one interval between occurrences of the events of the parametr not of interest;
   (d) filtering the signal components out from the measurement signal by generating a filtered measurement signal by forming a successon of mean values of the measurement signal, each mean value being formed from the most recent samples taken during a time span equal in length to the interval, a mean value being formed at each sampling; and
   (e) administering therapy to said life form having at least one variable therapy feature and controlling said variable therapy feature dependent on said filtered measurement signal.

2. The method of claim 1, wherein the measurement signal is an analog signal.

3. The method of claim 1, wherein the succession of mean values are calculated over overlapping time spans.

4. The method of claim 3, wherein the time spans are variable.

5. The method of claim 1 comprising the steps of:
   storing the samples in a shift register such that the samples are shifted into and through the register in chronological order;
   counting the samples taken between occurrences of the events;
   generating a pointer that identifies a range of samples taken since the last occurrence of an event; and
   generating the mean value by summing all samples within the range identified by the pointer and dividing such sum by the number of samples in the range identified by the pointer.

6. The method of claim 5, wherein the pointer is adjusted to identify a different range of samples when the number of samples taken since the last occurrence of an event differs from the number of samples identified by the pointer previously.

7. The method of claim 1, wherein the step of filtering the measurement signal comprises:
   sampling the measurement signal and storing samples thus obtained in chronological succession in a shift register;

detecting occurrences of events whose signal components are to be filtered out of the measurement signal;

counting the number of samples taken of the measurement signal since the last occurrence of such an event;

storing the count in a pointer memory upon the occurrence of such an event before the counting recommences; and continuously generating a mean value of the measurement signal by summing the latest samples as determined by the current count in the pointer memory and dividing the sum by the count in the pointer memory.

8. The method of claim 1, comprising identifying intervals between occurrences of the signal components of the parameter not of interest and forming each mean value from the most recent samples taken during a time span equal in length to the last identified interval.

9. The method of claim 8, comprising varying the intervals.

10. An apparatus for measuring a physiological function parameter of a life form, comprising:

a measurement circuit configured to sense a physiological function and to generate a measurement signal with signal components relating to respiration and activity of a heart in said life form;

a heart beat detector for detecting beats of said heart;

a filter circuit coupled to the measurement circuit and the heart beat detector and configured to generate a filtered signal as a measure of the physiological function parameter, the filter circuit including a sampling circuit configured to sample the measurement signal at a prescribed frequency and to generate a succession of signal samples, a clock configured to generate a clock signal with the prescribed sampling frequency, a shift register coupled to the sampling circuit and configured to store the samples in chronological succession, a counter coupled to the clock signal and to the heart beat detector so as to count samples taken between occurrences of heart beats, a pointer register coupled to the counter and configured to store the value of the counter just after the last occurrence of a heart beat before the counter is reset to zero, and a calculating stage coupled to the shift register, the pointer register and the clock signal and configured to sum a range of the samples in the shift register commencing from the latest sample to the earliest sample indicated by the value in the pointer register and generating a mean value of such samples; and means for administering therapy to said heart having at least one variable therapy feature and including means for controlling said variable therapy feature dependent on said filtered signal.

11. The apparatus of claim 10, wherein the apparatus is a heart pacemaker and wherein said means for administering therapy comprises means for generating stimulation pulses and for delivering said stimulation pulses to said heart.

12. A method for measuring a parameter of interest of a physiological function of a life form, comprising the steps of:

(a) acquiring a useful measured signal that is dependent on a function parameter and which includes occurrences of another function parameter;

(b) filtering out of the measured signal components relating to said another function parameter to obtain a filtered measured signal by continuously identifying a period duration occurring between the last two occurrences of the another function parameter, and continuously generating a mean value of the measured signal over the period duration; and (c) administering therapy to said life form having at least one variable therapy feature by using said mean value of the measured signal over the period duration as said filtered measured signal and controlling said variable therapy feature dependent on said filtered measured signal.

13. The method of claim 12, wherein said another function parameter comprises individual events that occur with the characteristic frequency, said method comprising detecting the events and calculating a current period duration of the another function parameter from the time elapsed between the two most recently detected events.

14. The method of claim 12, comprising varying the period duration.

* * * * *